United States Patent [19]
Siiman et al.

[11] Patent Number: 6,074,884
[45] Date of Patent: Jun. 13, 2000

[54] STABLE PROTEIN-NICKEL PARTICLES AND METHODS OF PRODUCTION AND USE THEREOF

[75] Inventors: Olavi Siiman, Davie; Alexander Burshteyn, Hialeah; John A. Maples, Miami Shores, all of Fla.; James Keller Whitesell, Austin, Tex.

[73] Assignee: Coulter International Corp., Miami, Fla.

[21] Appl. No.: 08/947,809

[22] Filed: Oct. 9, 1997

[51] Int. Cl.⁷ .................................................. G01N 33/533
[52] U.S. Cl. ...................... 436/518; 427/2.11; 427/2.13; 427/2.14; 427/131; 427/213.35; 427/215; 427/216; 427/337; 427/338; 428/403; 428/407; 435/5; 435/7.21; 436/524; 436/525; 436/526; 436/529; 436/531; 436/532; 436/533; 436/534
[58] Field of Search .................................. 427/2.11, 2.13, 427/2.14, 131, 213.35, 215, 216, 337, 338; 428/403, 407; 435/5, 7.21; 436/518, 524, 525, 526, 529, 531, 532, 533, 534

[56] References Cited

U.S. PATENT DOCUMENTS 5,466,609  11/1995  Siiman .
5,576,185  11/1996  Coulter .

OTHER PUBLICATIONS

S. Wong, "Chemistry of Protein Conjugation and Cross–Linking", CRC Press, Inc. (1991).

G. Hermanson, "Bioconjugate Techniques", Academic Press (1996).

M. Aslam et al, "Bioconjugation—Protein Coupling Techniques for the Biomedical Sciences", Grove's Dictionaries, Inc. (1998).

Pierce Catalog & Handbook, "Cross–Linking", Technical Section.

M. Sharrock, "Particulate Recording Media", MRS Bulletin, pp. 53–61 (Mar., 1990).

R. White, "Opportunities in Magnetic Materials", Science, 229 (4708):11–15 (Jul. 5, 1985).

C. Kittel et al, "Ferromagnetic Domain Theory", in Solid State Physics, F. Seitz and D. Turnbull, eds., vol. 3, pp. 437–564, New York, NY (1956).

K. Suslick, "Applications of Ultrasound to Materials Chemistry", MRS Bulletin, pp. 29–34 (Apr., 1995).

J. Whitesell et al, "Directionally Aligned Helical Peptides on Surfaces", Science, 261:73–76 (Jul. 2, 1993).

*Primary Examiner*—Christopher L. Chin
*Assistant Examiner*—Bao-Thuy L. Nguyen
*Attorney, Agent, or Firm*—Mary E. Bak

[57] ABSTRACT

A stable protein-coated nickel particle useful in biological assays contains a nickel particle having removed from the surface thereof nickel oxide; a linker attached to said nickel particle, the linker having a free amino group; and a protein attached to said linker by covalently bonding to the free amino group. Methods of producing and using these oxide-free nickel-protein conjugates are disclosed.

9 Claims, 2 Drawing Sheets

STABLE PROTEIN-NICKEL PARTICLES AND METHODS OF PRODUCTION AND USE THEREOF

FIELD OF THE INVENTION

This invention generally relates to novel magnetic beads useful in flow cytometry and cell separation protocols. More particularly, the invention relates to novel nickel particles, in which a protein is conjugated to a nickel particle free of nickel oxide, and methods of preparation and use thereof.

BACKGROUND OF THE INVENTION

Various magnetic beads useful for depletion of targeted cells are commercially available [see, e.g., U.S. Pat. No. 5,466,609]. However, metallic particles in magnetic applications [M. P. Sharrock, "Particulate Recording Media", in MRS Bulletin (March 1990), pp. 53–61; R. M. White, Science, 229:11–15 (1985)] display an undesirable tendency towards oxidation or other reactions caused by the elemental state of the metal combined with the high specific surface area common to all small particles. Thus, presently the magnetic beads with superior performance in immunomagnetic separations are DYNABEAD M-450® 4.5 micron diameter beads (DYNAL, Inc., Great Neck, N.Y.) which consist of monosized polystyrene particles embedded with ferrofluid $\gamma$-$Fe_2O_3$ particles. These magnetic beads can be effectively used at a 3–10 bead-to-cell ratio in positive cell selection and at a 10–40 bead-to-cell ratio in negative cell selection.

One type of metallic bead which is commonly employed is elemental nickel. Such nickel particles exhibit somewhat different ferromagnetic properties depending upon their size, either above or below about 20 nm diameter [C. Kittel and J. K. Gait, "Ferromagnetic Domain Theory", in Solid State Physics, F. Seitz and D. Turnbull, eds., Academic Press, New York, N.Y. (1956), Vol. 3, pp. 437–564]. Typical Raney (porous) nickel particles are produced on an industrial scale as a hydrogenation catalyst by thermal decomposition of nickel tetracarbonyl, and have an average diameter of 100 to 200 microns. Smaller particles in the 1 to 10 micron diameter range are also available.

Several methods have been employed to overcome the disadvantage of oxide formation as mentioned above. For example, nickel oxide layers on nickel particles can be removed by heat treatment. However, in order for decomposition of nickel oxide to its constituent elements in their standard states to be thermodynamically favorable, i.e., to have a negative standard free energy change, the temperature must be raised above 2540° K or 2270° C., otherwise nickel oxide remains unchanged. This can be shown with standard entropy and enthalpy data [$S°$ (Ni, s)=29.9 $JK^{-1}$ $mol^{-1}$, $S°$ ($O_2$, g)=205.0 $JK^{-1}$ $mol^{-1}$, $S°$ (NiO, s)=38.0 $JK^{-1}$ $mol^{-1}$, $\Delta H_f°$ (NiO, s)=−239.7 $kJmol^{-1}$, $\Delta H_f°$ (Ni, s)=$\Delta H_f°$ ($O_2$, g)=0] from CRC HANDBOOK OF CHEMISTRY AND PHYSICS, 64th ed., 1983–1984, CRC Press, Inc., Boca Raton, Fla., pp. D-50-D-93, which give $\Delta S°$ (reaction)=29.9+1/2(205.0)−38.0=94.4 $JK^{-1}$ $mol^{-1}$ or 0.0944 $kJK^{-1}$ $mol^{-1}$ and $\Delta H°$ (reaction)=0.0+0.0−(−239.7)= 239.7 $kJmol^{-1}$. Then, using the Gibbs-Helmholtz equation, $\Delta G°$ (reaction)=$\Delta H°$ (reaction)−$T\Delta S°$ (reaction), to find the temperature at which the standard free energy change reverses sign, $\Delta G°$ (reaction)=0=239.7−T(0.0944), and T=239.7/0.0944=2540 K.

Alternatively, such metallic particles can be stabilized by using alloying elements and additives, by protective organic coating, and by controlled oxidation of their surfaces, i.e., passivation. For example, antibody has been adsorbed onto nickel beads and then fixed thereon by crosslinking it with glutaraldehyde [U.S. Pat. No. 5,576,185, issued Nov. 19, 1996]. Attempts were made to enhance the nickel oxide layer with passivation by heat treatment at 250° C. to sterilize the beads and create more surface area for adsorption of antibody. An oxide coating on elemental solid nickel has long been used as a protective measure to prevent corrosion. Heating the nickel beads reduced the solubilization of nickel ions from the particles and did not alter the depletion performance of the antibody-coated beads.

Nevertheless, a high level of leaching, about 100 mg nickel/mL of 25% w/v solids nickel beads after 16 weeks storage at 5° C., of nickel ions from antibody-coated nickel beads suspended in bovine serum albumin (BSA) buffer still took place. Nickel oxide surfaces constantly exposed to buffered aqueous solution, unlike nickel surfaces exposed to air, are not immune to corrosion.

Thus, there exists a need in the art for compositions and methods which enable more efficient production and use of magnetic reagents for biological assays.

SUMMARY OF THE INVENTION

In one aspect, the invention provides a stable protein-conjugated nickel particle comprising:

(a) a nickel particle having removed from the surface thereof nickel oxide;

(b) a linker attached to said nickel particle, said linker having a free amino group; and (e) a protein attached to said linker by covalently bonding to said free amino group.

In another aspect, the invention provides methods for preparing the above-described particles, including methods which employ ultrasonication to prepare oxide-free nickel particles and an aminotrithiolate linker, to enable stable conjugation of protein to the nickel particles.

In still another aspect, the invention provides methods for performing magnetic separations or separations by gravitational sedimentation of two or more subpopulations of cells in a biological solution or suspension, such as whole blood, using the above-described nickel particles.

Other aspects and advantages of the present invention are described further in the following detailed description of the preferred embodiments thereof, reference being made to the accompanying figures.

DETAILED DESCRIPTION OF THE INVENTION

Figure 1:
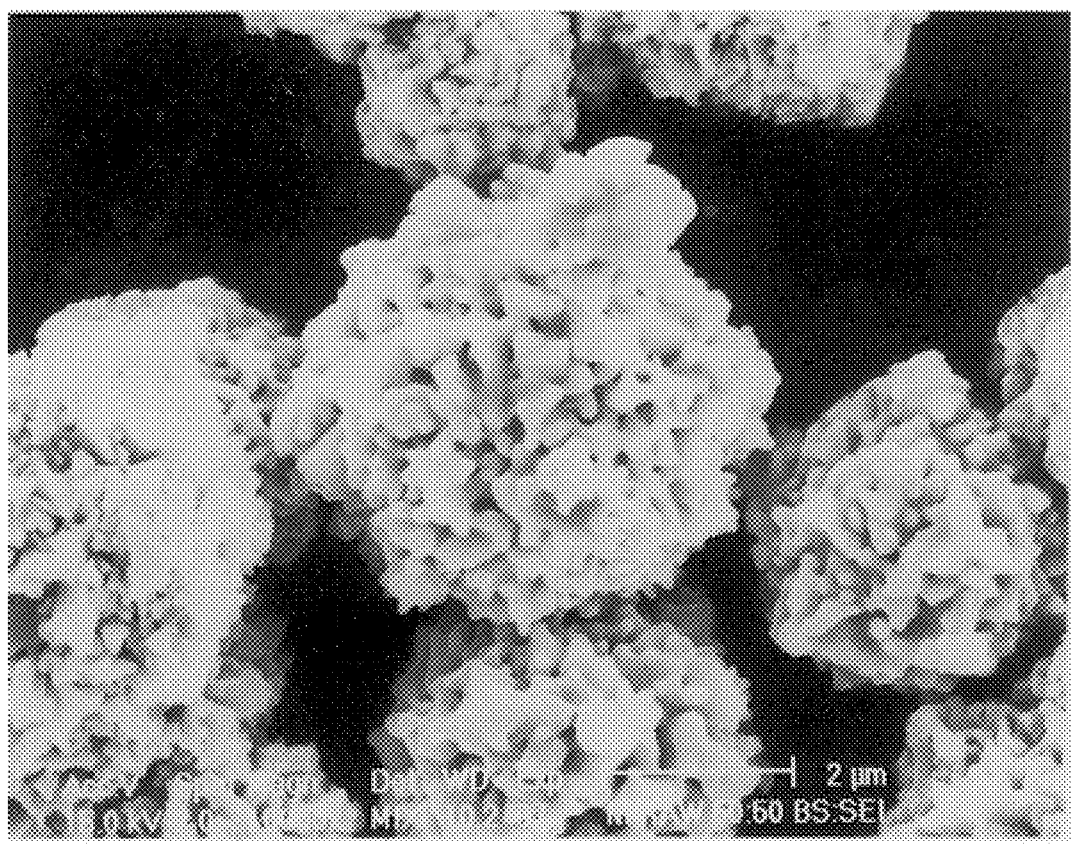
FIG. 1 is a scanning electron micrograph (SEM) photograph of raw nickel beads taken with 15.0 kV electron beam at 10,000× magnification, and 50/50 mixed detection of backscatter/standard emission.

The present invention meets the need in the art by providing protein-coated nickel particles and a novel method for preparing the nickel particles. These particles are then used in a variety of biological assays, particularly those involving magnetic separation or sedimentation of subpopulations of cells or other proteinaceous materials in a biological fluid.

I. Definitions

The term "particle", also includes inter alia, microspheres, beads and spheres and such terms are interchangeable.

"Antibody" is defined to include polyclonal antibodies from any native source, and native or recombinant monoclonal antibodies of classes IgG, IgM, IgA, IgD, and IgE, hybrid derivatives, humanized or chimeric antibodies, and fragments of antibodies including Fab, Fab', and F(ab')$_2$.

II. Compositions and Methods of the Invention The present invention provides a novel stable protein-conjugated nickel particle comprising:

(a) a nickel particle having removed from the surface thereof nickel oxide;

(b) a linker attached to said nickel particle, said linker having a free amino group; and (e) a protein attached to said linker by covalently bonding to said free amino group.

In a preferred embodiment, the particles of the present invention comprise oxide-free nickel beads coated with a bifunctional aminothiolate spider ligand. Protein, preferably antibody, is attached to the coated particles through the activated ligand. These conjugates are particularly advantageous in that they enable the analyses of at least two different subsets of protein-bearing materials, e.g., two subsets of T lymphocytes in a biological material containing white blood cells, via magnetic separation or gravitational sedimentation.

The method of this invention involves removing from commercially available nickel beads the oxide coating; attaching a stabilizing bifunctional linker to the cleaned nickel surface; and conjugating protein, e.g., antibody, covalently to the linker.

A. The Nickel Bead Substrate and Its Preparation

The elemental nickel bead or particle useful in this invention preferably ranges in size from between about 3 to about 10 microns in diameter (i.e., colloidal-sized). Such nickel beads generally contain on the surface thereof, nickel oxide, or are subject to nickel oxide formation. Such nickel beads are commercially available, e.g., from sources such as Novamet Specialty Products Corp, Wyckoff, N.J.; alternatively nickel particles of a desired size may be produced from nickel powder by means known to the art. See, e.g., the about 7.4 μm particles used in Example 1; see also U.S. Pat. No. 5,576,185, which discloses beads of about 4.1–5.7 μm.

As part of this invention, the commercially available nickel beads are cleaned to remove nickel oxide from the nickel surface. Ultrasonication has recently been used to obtain clean, reactive metal surfaces [K. S. Suslick, "Applications of ultrasound to materials chemistry", MRS Bulletin (April 1995), pp. 29–34, and references therein]. In this published description of the chemical effects of ultrasound on solids and surfaces, it was shown that one of the "world's worst" heterogeneous catalysts, Raney nickel right out of the bottle, could be irradiated with ultrasound to increase its reactivity by more than 100,000-fold and regain Raney nickel-like activity. Auger depth profiling showed that the deep, passivating oxide coating on nickel particles before sonication was removed by irradiation with ultrasound.

Thus, ultrasonication is employed as the method of cleaning nickel bead surfaces to remove the nickel oxide coating. Desirable parameters for the sonochemical apparatus include use of a maximum amplitude for about 8 hours, and other conventional conditions are described in Suslick, cited above and incorporated by reference; and in Example 1.

B. The Bifunctional Linker

Once cleaned, the nickel surface of the bead must be made receptive to conjugation with protein, e.g., antibody. Preferably to prepare stable protein-nickel bead conjugates useful in biological cell assays, selected protein(s) are covalently conjugated to chemically-reactive groups on the surface of the cleaned nickel beads. One way of accomplishing this conjugation to the nickel bead surface is to use a bifunctional linker molecule, part of which can be strongly attached to nickel on the particles, while a different part of the linker can be chemically activated to allow conjugation of antibody. The three sulfur atoms of the linker bind strongly to the metal on the substrate.

A preferred linker is an aminotrithiolate linker. A particularly useful aminotrithiol linker is tris(3-mercaptopropyl)-N-glycylaminomethane, a spider-like composition having the composition $C_{12}H_{26}N_2OS_3$, and structural formula, $H_2NCH_2CONHC(CH_2CH_2CH_2SH)_3$ [J. K. Whitesell and H. K. Chang, *Science*, 261: 73–76 (1993)]. See the structure below:

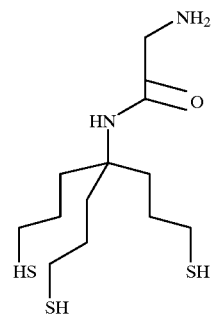

This compound was originally described as forming a layer on a roughened gold film surface, to provide $NH_2$ initiation sites for polymerization of alanine N-carboxyanhydride to form polyalanine helices that uniformly aligned themselves perpendicular to the surface. The polyalanine helices were shown to remain attached to the gold surface and retain their conformation even after heating to 180° C. for one week.

The preferred form of this linker is the freshly deprotected form, which is preferably prepared as described in detail in Example 2 below. The aminotrithiol linker functions well as a ligand between nickel particles and monoclonal antibodies. The three soft base, highly polarizable sulfur atoms of low electronegativity of the ligand coordinate strongly to the soft acid, i.e., nickel atoms on cleaned nickel bead surfaces. Thus, this linker allows activation and conjugation of antibody through its amino group. The aminotrithiol linker also serves as a new bifunctional linking agent.

The linker as described above is covalently bonded to the cleaned nickel particle. The aminotrithiol linker may be attached by reaction of thiolate groups with the nickel surface. More specifically, the method of using the aminotrithiol linker comprises dissolving protected aminotrithiol ligand in anhydrous methanol; adding concentrated hydrochloric acid to the resulting solution; and refluxing the mixture. In one embodiment a preferred time for refluxing is about 5 hours. The components of the mixture are separated, e.g., by size exclusion chromatography on a BioGel P2® gel, and fractions of the first band (representing deprotected aminotrithiol ligand) absorbing at 280 nm, are collected. The deprotected aminotrithiol ligand is then mixed with the nickel beads described above. Thus strong covalent bonds are formed between the sulfur groups on the linker and the nickel atoms on the bead surface.

C. Activation of Linker

For activation of the free amino groups of the linker on the particles, a heterobifunctional cross-linking agent, such as sulfosuccinimidyl 4-[N-maleimidomethyl] cyclohexane-1-carboxylate ("sulfo-SMCC") is used. Sulfo-SMCC covalently bonds to the linker with reactive amino groups. Various other suitable crosslinking agents and methods are cited in texts such as The Pierce Handbook and *Chemistry Of Protein Conjugation And Cross-Linking*, S. S. Wong, CRC Press, Inc., Boca Raton, Fla. (1991).

To be successful, the activation method, such as sulfo-SMCC for amino groups of the linker-coated nickel beads should not disturb the attachment of linker to the nickel beads or the single, dispersed particle status of the beads.

D. The Protein

Once the crosslinker is attached to the particle, a selected protein which is desired to be attached to the particle is then conjugated to the amino groups of the activated linker on the coated particles by conventional methods, e.g., by activating the protein with an amino binding reagent which provides a sulfhydryl group. A suitable amino binding/activating reagent is 2-iminothiolane. Conventional methods of 2-iminothiolane activation of antibody and maleimide (sulfo-SMCC) activation of amino groups on coated particles to conjugate antibody to particles, are described in *Chemistry Of Protein Conjugation And Cross-Linking*, S. S. Wong, CRC Press, Inc., Boca Raton, Fla., 1991. Still other amino-reactive sulfhydryl introducing reagents may readily be selected by one of skill in the art from available texts [See, also, Pierce Handbook].

The protein attached through the crosslinker to the linking agent on the nickel particle to form the novel, stable protein-coated nickel particle of the invention is preferably an antibody. More specifically, the protein is covalently bonded to the linker-nickel particle by covalent bonding of the free amino groups on the linker through the heterobifunctional crosslinker with sulfhydryl or amino groups on the activated protein.

Although any protein may be attached to the substrate in this way, preferably, the protein is a monoclonal or polyclonal antibody or any one of a variety of recombinant antibody constructs. The antibody is desirably directed to an epitope on a cell, which epitope is unique to the cell type, thereby permitting the particle's use in cell separation assays. Polyclonal antibodies may be generated by conventional means, i.e., obtained from sera of animals or humans exposed to a selected antigen. For example, polyclonal antibodies are generated by conventionally stimulating the immune system of a selected animal or human with a selected antigen, allowing the immune system to produce natural antibodies thereto, and collecting these antibodies from the animal or human's blood or other biological fluid.

Monoclonal antibodies are obtained by conventional hybridoma methods and purified from ascites fluid by ammonium sulfate (45%) precipitation, centrifugation and affinity chromatography using protein A. Processes of making monoclonal antibodies are described in G. Kohler and C. Milstein, *Nature*, 256:495–497 (1975) and include the many known modifications thereof, which teachings are incorporated herein by reference. Similarly desirable high titer antibodies are generated by applying known recombinant techniques to the monoclonal or polyclonal antibodies developed to these antigens [see, e.g., PCT Patent Application No. PCT/GB85/00392; British Patent Application Publication No. GB2188638A; Amit et al., *Science*, 233:747–753 (1986); Queen et al., *Proc. Nat'l. Acad. Sci. USA*, 86:10029–10033 (1989); PCT Patent Application No. PCT/WO9007861; and Riechmann et al., *Nature*, 332:323–327 (1988); Huse et al, *Science*, 246:1275–1281 (1988)a].

One of skill in the art may generate chimeric, humanized or fully human antibodies for use as the protein of this invention by resort to known techniques by manipulating the complementarity determining regions of animals or human antibodies. See, e.g., E. Mark and Padlin, "Humanization of Monoclonal Antibodies", Chapter 4, *The Handbook of Experimental Pharmacology*, Vol. 113, The Pharmacology of Monoclonal Antibodies, Springer-Verlag (June, 1994).

Of course, the particular method of making and the type of antibody is not limited to such techniques and it is envisioned that any technique for making such antibodies is within the practice of the invention. In a preferred embodiment, the protein is a monoclonal antibody to the CD3, CD4 or CD8 receptor on T lymphocytes. Examples of such monoclonal antibodies are the following: monoclonal antibody (MAb) "T3" (commercially available from Coulter Corporation, Miami, Fla.) is an anti-CD3 antibody of IgG1 subclass, derived from the hybridization of mouse P3/NS1/1-AG4-1 myeloma cells with spleen cells from BALB/c mice immunized with human infant thymocytes and peripheral blood lymphocytes from a patient with Sezary cell leukemia.

MAb "T4" (Coulter Corporation) is an anti-CD4 antibody derived from hybridization of mouse NS/1-AG4 cells with spleen cells of BALB/cJ mice immunized with human peripheral blood T lymphocytes. MAb "T8" is an anti-CD8 antibody, derived as described for T4, but immunized with human thymocytes (Coulter Corporation). MAbs T4 and T8 are chosen for use in the examples below for the large density of their antigenic receptors ($10^4$–$10^5$ receptors per targeted cell) and the mutual exclusiveness of their targeted cells.

However, as the protein portion of the novel particle, any antibody directed against any targeting receptor site on a cell may be used, as long as the sites per cell are greater than about $10^3$ and each such site is exclusive to one cell population in multiple targeted cell populations.

The activated linker coated nickel particle is purified and the activated protein is purified, both by conventional means. The purified particles in aqueous suspension are then mixed with an amount of an aqueous solution of the activated protein sufficient to saturate the reactive groups on the activated particles. This mixing preferably occurs at room temperature and for a time sufficient to permit conjugation between the protein and particle, resulting in a stable particle. Selection of the amount of the activated protein solution and the mixing times are clearly within the skill of the art, depending upon the amount of particle to be conjugated to protein, and these parameters are limitations of this method.

Preferably, before use, unreacted functional groups on the resulting stable particles are blocked with appropriate blocking agents, such as L-cysteine and iodoacetamide. For use in biological assays, exemplary particles of the invention, e.g., antibody-conjugated aminothiolate coated nickel particles, may be suspended in suitable buffers, such as bovine serum albumin (BSA) buffer.

III. Methods of Use

The protein-conjugated nickel beads described herein can be used either in magnetic separations or as heavy beads in separations by gravitational sedimentation [see, e.g., U.S. Pat. No. 5,576,185]. For example, one exemplary method employing the particles of the invention demonstrates the quantitative determination of a subpopulation of white blood cells in a biological solution/suspension containing both red blood cells and white blood cells.

Thus, a method of the present invention comprises the steps of mixing a biological solution or suspension, e.g., whole blood, with stable particles as described above. Each particle contains a protein, e.g., an antibody, conjugated thereto that binds to an epitope on a subpopulation of cells, e.g., white blood cells. The particles and biological material are mixed for a time sufficient to permit the binding of the particles to the targeted subpopulation of cells, upon which the targeted cells are removed by magnetic separation or by sedimentation.

Thereafter, the red blood cells in the biological solution/suspension are lysed and quenched. This mixture is analyzed in an instrument that enumerates undepleted white blood cells, and, by the difference between the original blood sample and the magnetic bead depleted sample, allows enumeration of depleted cells.

By such a method, one may quantitatively detect subpopulations of white blood cells, such as $CD4^+$ T lymphocytes ("T4 cells"), $CD8^+$ T lymphocytes ("T8 cells")), B lymphocytes, granulocytes, basophils, and monocytes, among others. The nickel beads of the present invention compare favorably with the Dynal® magnetic antibody-conjugated beads described in the Background above at bead-to-cell ratios of between 3 and 22, and with ferrite beads (U. S. Pat. No. 5,466,609) which provided bead-to-cell ratios of between 77 and 4900 for depletion of all RBCs and WBCs, respectively.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLE 1

Cleaning of Raw Nickel Beads by Ultrasonication 50 g of nickel powder (INCO, Suffern, N.Y.) type 123 ($d_{50}$=7.4 μm, 2.42 g/cm$^3$ density, 0.50 m$^2$/g specific surface area) was prepared by decomposition of nickel tetracarbonyl (Novamet Specialty Products Corp., Wyckoff, N.J.). The resulting beads were suspended in 200 mL of 0.2 mm-filtered distilled water (DW) in a 250 mL tube. The mixture was roller mixed overnight, magnetically separated, and the supernatant containing fine particles was discarded. The residue was resuspended in 200 mL of DW in a 400 mL Pyrex® jacketed beaker, which was thermostated at a setting of 0° C. with a chilled, circulating 1:1 mixture of ethylene glycol-water from a Forma Scientific® model 2006 circulator/cooler.

The suspension of nickel beads in the jacketed beaker was then sonicated with a Braun Sonic 2000® ultrasonic probe set at maximum amplitude for efficient mixing of nickel beads for 8 hours. During this period and at the end of the sonication period the supernatant was separated from the nickel beads, discarded, and the residue resuspended in 200 mL of fresh DW 3–4 times.

EXAMPLE 2

Deprotection of t-BOC Spider Triacetate Linker Ligand

The cross-linker, $C_{12}H_{26}N_2OS_3$, was prepared substantially as described in Whitesell & Chang [Science 261, 73 (1993)] and stored as the protected ligand, N-tert-butoxycarbonyl spider triacetate.

10 mg of protected ligand was dissolved in 5 mL of anhydrous methanol to give a colorless solution. 2.5 mL of concentrated hydrochloric acid (36.5–38.0%) was then added to the solution of protected spider. The mixture was refluxed in a 50 mL round bottom flask for 5 hours to give a yellow solution having the odor of free sulfhydryl groups. The acid-catalyzed hydrolysis mixture (final volume of 3.0 mL) of spider ligand was applied to the top of a Bio-Gel® P-2 column, 1.1 cm×30 cm, and eluted with DW.

Fractions of the first band absorbing at 280 nm were collected and tested with Ellman's reagent, 5,5'-dithio-bis-[2-nitrobenzoic acid], against a phosphate buffer blank. The reagent reacts with free sulfhydryl groups to form a highly colored chromophore with an absorbance at 412 nm [J. C. Ellman, Clin. Chem. Acta, 28:234–241 (1962)]. Fifteen minutes were allowed for development with Ellman's reagent.

For a quantitative determination of sulfhydryl groups, a standard curve was run for L-cysteine to determine the linear response range for the complex. Twelve deprotected ligand fractions of 56 mL total volume gave an $A^{412}$ reading of 0.549 or sulfhydryl concentration of 0.458 mM, representing a yield of 44%.

EXAMPLE 3

Coating of Cleaned Nickel Beads with Deprotected Spider Ligand

Three trials with 0.01, 0.003, and 0.001 mM sulfhydryl concentration of spider and 5 mL of 25% w/v solid nickel beads, stored in DW purged with nitrogen gas in a refrigerator at 5° C. were prepared. Required volumes of 0.109, 0.033, and 0.011 mL of 0.458 mM spider sulfhydryl groups were added to nickel bead suspensions after removing equal volumes of supernatant. The trial samples in 50 mL tubes were purged with nitrogen gas and roller mixed overnight for 16–24 hours.

Each sample was then washed five times with 1×PBS and resuspended to 5 mL with 1×PBS.

EXAMPLE 4

Conjugation of T8 Antibody to Coated Nickel Beads 1.5 mL of 10 mg/mL sulfo-SMCC solution were used per mL of 1% w/v solids of coated nickel beads to activate the aminotrithiolate-coated nickel beads. Thus, 0.375 mL sulfo-SMCC solution was added to each trial sample, which were then roller mixed for one hour with occasional brief sonication. All trials were washed five times with 1×PBS buffer solution and resuspended to 10 mL total volume with 1×PBS.

30 mg of T8 (0.799 mL) antibody concentrate in 1.007 mL of 1×PBS buffer solution were activated with 2-iminothiolane(IT) at a 15:1=IT: Ab molar ratio, using 0.194 mL of 2 mg/mL IT solution. The reaction mixture in a 15 mL polystyrene centrifuge tube was roller mixed for one hour, and then applied to the top of a 60 mL G-50 Sephadex column, equilibrated with 1xPBS. The column was eluted with 1×PBS, and fractions of the first $A^{280}$-absorbing band containing IT-T8 were pooled to yield 7 mL of 3.864 mg/mL IT-T8 antibody solution.

Conjugations were run at 0.8 mg IT-T8/mL of 25% w/v solids beads, so that 2.070 mL of IT-T8 solution were added to each of the three samples of 10 mL of sulfo-SMCC-activated nickel beads after removal of 2.070 mL of supernatant from each bead suspension. The mixtures were roller mixed for two hours, and at the end of the conjugation period, 1 mL of each mixture was pipetted and filtered through an 0.2 μm low-protein binding filter disc.

The $A_{280}$ of each supernatant was measured to yield supernatant IT-T8 concentrations of 0.160, 0.182, and 0.364 mg/mL, respectively. By difference, the surface concentrations of IT-T8 were 0.640, 0.618, and 0.436 mg/mL or 5.12, 4.94, and 3.49 mg T8 antibody/m² of bead surface area, respectively, using the specific surface area of 0.50 m²/g quoted by the manufacturer. The samples were blocked with 1.08 mL of 5 mg/mL L-cysteine solution in 1xPBS (15 minutes), and then, 1.21 mL of 20 mg/mL iodoacetamide solution in 1xPBS and 0.230 mL of 1M borate buffer solution, pH 9.8 (30 minutes). At the end of the blocking reactions, all three bead samples were separated by sedimentation, the supernatants were discarded, and the residues were washed three times with BSA buffer, 1%BSA/ 0.1% sodium azide in 1xPBS solution, resuspended in BSA buffer, roller mixed for one hour, and stored in a refrigerator at about 5° C. for 16–24 hours. The samples were then further washed three times with BSA buffer and the total volume of each sample was adjusted to 10 mL.

EXAMPLE 5

Analyses of Supernatants of T8-nickel Bead Suspensions for Free Antibody and Nickel Ions The average nickel contents of supernatants of T8-nickel beads stored at 5° C., room temperature, or 37° C. for 16 weeks were 29.7, 48.6, and 59.1 µg/mL, respectively. ELISA analyses of supernatants for $IgG_1$ antibody initially gave results of 0.719, 0.803, and 0.493 µg/mL, respectively and then gave results of 5.10, 5.23, and 3.82 µg/mL, respectively, after sixteen weeks at 5° C. for three T8-nickel bead samples.

These results demonstrate that if the amount of supernatant antibody is too large, the beads will fail to deplete the targeted cell. If supernatant antibody amounts are small, more beads may be needed for target cell depletion; alternatively, the beads can be washed before using in the depletion.

EXAMPLE 6

Scanning Electron Micrographs of Nickel Beads

Samples of raw nickel beads suspended at 25% w/v solids in distilled water and sonicated nickel bead suspension were prepared for scanning electron microscope (SEM) viewing by applying one drop of suspension to a metal stub coated with black conducting tape, spreading and removing most of the droplet with a pipet, and air-drying the remainder of the applied sample.

Figure 2:
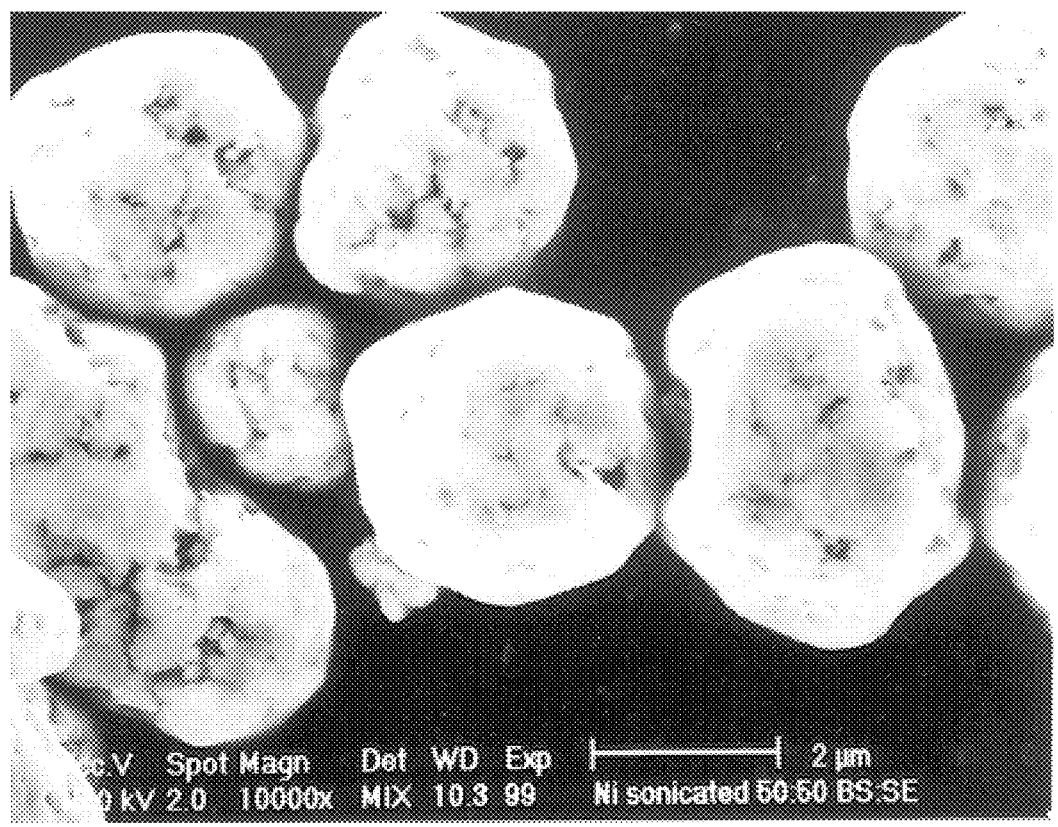
FIG. 2 is an SEM photograph of sonicated nickel beads taken under the same conditions as FIG. 1.

SEM photos were taken using a Philips Model XL40 FEG instrument. FIGS. 1 and 2 show SEM photos of raw nickel beads and sonicated nickel beads, respectively, taken with a 15.0 kV electron beam at 10,000× magnification, and 50/50 mixed detection of backscatter/standard emission. The raw beads of about 4 to 5 micron diameter showed a corrugated, crystallite surface of high surface area, which was smoothened on the macroscopic scale by sonication to yield nickel beads of about one micron smaller in diameter. This decrease in particle size can be related to previous Auger depth profiling [K. S. Suslick, MRS Bulletin, April 1995, 29–34] which showed a deep oxide coating before sonication and removal of the passivating nickel oxide layer after irradiation with ultrasound.

EXAMPLE 7

Protocol for Nickel Bead Depletion of T8-cell Populations

Whole blood samples for T8-cell depletion experiments were prepared as follows. T8-linker-nickel bead suspensions were obtained from 25% w/v solids, with dilution with 1xPBS when needed, as 1, 5, 10, 15, and 25% w/v solids suspensions. Ten microliters of each suspension was used per 100 mL of whole blood from two donors. Undepleted controls contained 10 mL of 1xPBS buffer.

The samples were then mixed on a Coulter model P1122 mixer for 2 minutes and magnetically separated with a multiposition Corning magnetic separator for 1 minute. All supernatants of depleted samples were transferred to matching tubes, to which were added 10 mL of Coulter CYTO-STAT® T4-RD1/T8-FITC fluorescent marker, mixed for 10 minutes and run on Coulter Q-PREP EPICS® immunology workstation model U13337, in 35 second cycles to lyse red blood cells and fix the cells.

For each of two donors three controls were prepared. The first contained no antibody marker and was used to establish the position of white blood cell scatter. The second, contained the dual fluorescent marker, Coulter CYTO-STAT® MsIgG1-RD1/MsIgG1-FITC, to determine background fluorescence, nonspecific cell fluorescence, and cell autofluorescence. PMT voltages were adjusted to give log (fluorescence) values for the latter in the range of 0.1 to 1.0. The third control contained the dual fluorescent label, Coulter CYTO-STAT® T4-RD1/T8-FITC, to establish overlap in emission spectra of the two labels and compensate for it. Each control consisted of 100 mL of whole undepleted blood from each donor and 10 mL of label or 1xPBS buffer, mixed gently for 10 minutes and run on a Coulter Q-PREP® instrument in 35 second cycles.

All depleted samples and two undepleted controls were analyzed on the Coulter EPICS Profile II® flow cytometer. Prior to runs, the flow cytometer was aligned with Coulter DNA CHECK® beads to give CV values less than 2.0%. Fluorescence intensity standardization was carried out with Coulter STANDARD-BRITE® beads to obtain mean channel values of fluorescence intensity in the range of +/− one channel of FITC, PE, and ECD intensity.

Fluorescent counts from the T8-FITC marker were recorded for undepleted samples and for T8-linker-nickel bead-depleted samples to determine the percentage depletion of T8 cells as [F1 counts, undepleted sample-F1 counts, depleted sample]/(F1 counts, undepleted sample)×100.

The % depletion results for 500 mL of whole blood and various titers of 2.5% w/v T8-nickel bead suspension are summarized in Table I.

TABLE I

| | lot 49-1 | | lot 49-2 | | lot 49-3 | |
|---|---|---|---|---|---|---|
| Bead Titer | % T8 + cells | % T8 cells depleted | % T8 + cells | % T8 cells depleted | % T8 + cells | % T8 cells depleted |
| 0 µL | 37.1 | 0 | 37.1 | 0 | 37.1 | 0 |
| 10 | 30.9 | 16.7 | 28.9 | 22.1 | 30.7 | 17.3 |
| 20 | 27.7 | 25.3 | 23.9 | 35.6 | 27.6 | 25.6 |
| 50 | 21.2 | 42.9 | 21.1 | 43.1 | 18.7 | 49.6 |
| 100 | 23.6 | 36.4 | 18.1 | 51.2 | 14.5 | 60.9 |
| 200 | 0.5 | 98.7 | 0.5 | 98.7 | 0.3 | 99.2 |
| 300 | 0.1 | 99.7 | 0.2 | 99.5 | 0.0 | 100 |

Bead-to-cell ratios were calculated from the average volume/nickel particle of $2.12 \times 10^{-10}$ cm³, and thus average mass per particle of $5.13 \times 10^{-10}$ g. Then, for 1 mL of 2.5% w/v solids nickel beads, or 0.025 g of nickel beads, there are $4.87 \times 10^7$ nickel particles/mL of 2.5% w/v solids beads. For a titer of 200 mL of 2.5% w/v solids beads, there are $9.74 \times 10^6$ beads, respectively.

Lymphocytes per mL of whole blood were enumerated on the Coulter STKS2B® hematology analyzer as $1.64 \times 10^3$ for one donor. For 500 mL of whole blood per sample, this gave $8.2 \times 10^5$ lymphocytes. Flow cytometry analyses of the undepleted samples produced 37.1% T8+ or $3.04 \times 10^5$ T8+ lymphocytes for this donor. Therefore, the bead-to-cell ratio was calculated as 32. Results of bead-to-cell ratios for other donors and T8-nickel bead runs varied between 3 and 32.

Similar trials with KC16 antibody-conjugated and linker ligand coated nickel beads showed that 400 mL of whole blood were 95.68% depleted of red blood cells by 500 mL of 50% w/v solids beads. The red blood cells were enumerated before ($4.60 \times 10^6$ RBC/mL of whole blood) and after depletion with KC16 beads on the Coulter STKS2BÔ hematology analyzer. There were $9.74 \times 10^8$ nickel particles per mL of 50% w/v solids beads, so that the titer of 500 mL of beads contained $4.87 \times 10^8$ nickel particles.

Also, the number of RBCs depleted from 400 mL of whole blood was $0.9568 \times 400$ mL $\times 4.60 \times 10^6$ RBC/mL= $1.76 \times 10^9$ RBC depleted. Therefore, the RBC-to-nickel bead ratio was 3.6.

All publications cited in this specification are indicative of the level of skill of those in the art to which this application pertains and are incorporated herein by reference.

While the invention has been described with reference to a particularly preferred embodiment, it will be appreciated that modifications can be made without departing from the spirit of the invention. Such modifications are intended to fall within the scope of the appended claims.

What is claimed is:

1. A stable protein-coated nickel particle useful in biological assays, consisting essentially of:
   (a) a nickel particle having removed from the surface thereof by ultrasonification nickel oxide;
   (b) a linker attached to said nickel particle, said linker having a free amino group; and
   (e) a protein attached to said linker by covalently bonding to said free amino group.

2. The particle according to claim 1, wherein said nickel particles (a) range in size from between about 3.0 to about 10.0 microns in diameter.

3. The particle according to claim 1, wherein said protein is an antibody.

4. The particle according to claim 3, wherein said antibody is selected from the group consisting of an anti-CD4 antibody and an anti-CD8 antibody.

5. The particle according to claim 3, wherein said protein is covalently bonded to the free amino groups of said linker by covalent bonding with sulfhydryl groups on 2-iminothiolane activated protein.

6. The particle according to claim 1 which is suspended in a buffer.

7. A stable protein-coated nickel particle useful in biological assays, consisting essentially of:
   (a) nickel particle having removed from the surface thereof nickel oxide;
   (b) an aminotrithiolate linker attached to said nickel particle, said linker having a free amino group; and
   (c) a protein attached to said linker by covalently bonding to said free amino group.

8. The particle according to claim 7 wherein said aminotrithiolate linker is tris(3-mercaptopropyl)-N-glycylaminomethane of formula $C_{12}H_{26}N_2OS_3$.

9. The particle according to claim 8, wherein said aminotrithiolate linker is covalently bonded to said nickel particles by covalent metal-sulfur bonds.

* * * * *